(12) United States Patent
Speaker

(10) Patent No.: US 8,685,425 B2
(45) Date of Patent: *Apr. 1, 2014

(54) MICROENCAPSULATION PRODUCT AND PROCESS

(76) Inventor: Tycho J. Speaker, Santa Cruz, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/274,842

(22) Filed: Oct. 17, 2011

(65) Prior Publication Data

US 2012/0034284 A1 Feb. 9, 2012

Related U.S. Application Data

(63) Continuation of application No. 11/792,727, filed as application No. PCT/US2005/044222 on Dec. 7, 2005, now Pat. No. 8,039,015.

(60) Provisional application No. 60/634,219, filed on Dec. 8, 2004.

(51) Int. Cl.
*A01N 25/28* (2006.01)

(52) U.S. Cl.
USPC ........... 424/417; 424/408; 424/418; 424/419; 424/420; 424/489; 424/496; 424/497; 424/498; 424/500; 424/502

(58) Field of Classification Search
USPC ........... 514/919, 937, 963; 424/408, 417, 418
See application file for complete search history.

(56) References Cited

U.S. PATENT DOCUMENTS

| | | | |
|---|---|---|---|
| 2,435,005 A | 1/1948 | Huppke et al. |
| 3,959,457 A | 5/1976 | Speaker et al. |
| 4,743,583 A | 5/1988 | Speaker et al. |
| 4,797,234 A | 1/1989 | Speaker et al. |
| 4,917,892 A | 4/1990 | Speaker et al. |
| 4,956,129 A | 9/1990 | Scher et al. |
| 5,093,198 A | 3/1992 | Speaker et al. |
| 5,132,117 A | 7/1992 | Speaker et al. |
| 5,284,663 A | 2/1994 | Speaker |
| 5,290,570 A | 3/1994 | Nichols |
| 5,490,986 A | 2/1996 | Speaker |
| 5,686,113 A | 11/1997 | Speaker et al. |
| 6,270,800 B1 | 8/2001 | Speaker et al. |
| 6,531,156 B1 | 3/2003 | Clark et al. |

*Primary Examiner* — Neil Levy
(74) *Attorney, Agent, or Firm* — RatnerPrestia

(57) ABSTRACT

Microcapsules possessing Lewis acid-Lewis base salt walls incorporate water-immiscible materials, such as N,N-diethyl-m-toluamide (DEET), as a core component. Such microcapsules, or similar microcapsules incorporating other core components, may be made by emulsifying a water-immiscible core component in an aqueous solution of one wall-forming reactant, such as the Lewis base, and then mixing that solution with the other wall-forming reactant, such as the Lewis acid. Various adjuvants may be included with the core component to contribute additional characteristics, such as enhancement of a controlled release characteristic or improved mechanical stability.

29 Claims, No Drawings

MICROENCAPSULATION PRODUCT AND PROCESS

This application is a continuation of U.S. application Ser. No. 11/792,727, filed Nov. 20, 2007, which is the National Phase filing of PCT Application No. US05/044222, filed Dec. 7, 2005, and claims priority of Provisional U.S. Application No. 60/634,219, filed Dec. 8, 2004, the entireties of which applications are incorporated herein by reference.

FIELD OF THE INVENTION

This invention relates generally to the encapsulation and controlled release of materials and to related encapsulated products and processes for making and using such products. Because capsules thus formed are generally of very small size, these products and processes are often referred to as microcapsules and microencapsulation processes.

BACKGROUND OF THE INVENTION

The use of droplets or particles of an active substance incorporated in an inactive carrier or carrier composition is well known in various arts including pharmaceutical, medical, agricultural, and many others. Typically, specific compositions provide for the application of specific active substances in a quantity or concentration appropriate to the use, and are particularly well suited to cases where the active substance itself is not easily compounded into a suitable vehicle or to facilitate controlled release of the active substance.

Encapsulation methods and materials are diverse and are well known to those skilled in the art of preparing controlled-release formulations. Encapsulation may take the form of an enclosing wall of inactive agent around a solid or liquid core of active agent, or it may take the form of a continuous matrix of porous inactive agent that contains the active, agent in the manner of a sponge or foam.

Among known encapsulation compositions and methods are those based on the formation of capsular walls by the reaction of a Lewis acid and a Lewis base, aligned at a droplet interface in an emulsified two-phase (generally aqueous-organic solvent) mixture, with a core material trapped in the droplet to be encapsulated. A number of such compositions and methods, and variants thereof, are disclosed in U.S. Pat. Nos. 3,959,457, 4,743,583, 4,797,234, 4,917,892, 5,093,198, 5,132,117, 5,284,663, 5,490,986, 5,686,113, 6,270,800, and 6,531,156, in all of which Dr. Tully Speaker is the inventor or a co-inventor and in some of which the present inventor is a co-inventor.

Other encapsulation methods are also known in the art. In general, many known methods have characteristics that may in some cases make them somewhat inconvenient to practice, such as a need for ultrasonication and/or use of organic solvents. Thus, alternative methods of encapsulation are desired in various technology areas.

SUMMARY OF THE INVENTION

In one aspect, the invention provides a method of making microcapsules containing a water-immiscible core material. The method includes:
(a) forming an emulsion including droplets of a water-immiscible core material in a first aqueous solution of an amphiphilic first wall-forming reactant that preferentially accumulates at the surface of the droplets;
(b) forming a second aqueous solution of a second wall-forming reactant; and
(c) combining the emulsion with the second aqueous solution to permit a reaction between the first and second reactants such that the resulting reaction product forms an encapsulating wall surrounding the core material of each emulsion droplet;
wherein one of said first and second reactants includes a Lewis base reactant and the other includes a Lewis acid reactant, and wherein the reaction product consists of a salt of the Lewis base-Lewis acid reactant pair.

In another aspect, the invention provides microcapsules including (a) a shell including the salt product of a Lewis acid reactant and a Lewis base reactant, and (b) contained within the shell, a core material including a vaporizable active agent.

In yet another aspect, the invention provides microcapsules including (a) a shell including the salt product of a Lewis acid reactant and a Lewis base reactant, and (b) contained within the shell, a core material including a flavorant.

In still another aspect, the invention provides microcapsules including (a) a shell including the salt product of a Lewis acid reactant and a Lewis base reactant, and (b) contained within the shell, a core material including a dye or colorant.

DETAILED DESCRIPTION OF THE INVENTION

Methods of forming microencapsulated materials according to the invention will now be described in detail, followed by a description of suitable materials for use in making the microencapsulated materials and then a description of methods for isolation and/or use of these materials.

Formation of Microcapsules

In one aspect of the invention, a water-immiscible core material, which may comprise an active agent, is encapsulated by a process in which the core material is emulsified in an aqueous solution of a first wall-forming reactant (one member of a Lewis acid-Lewis base reactant pair) to form dispersed droplets of the core material in the solution. The core material comprises an active agent, an adjuvant, or both, as will be described in detail later herein.

The reactant in the first mixture must be amphiphilic, i.e. having both hydrophilic and lipophilic moieties. Without wishing to be bound by any particular theory or explanation, it is thought that forces of polar solvent interaction drive the lipophilic end to solvate into the less-polar interior of the droplet, leaving the hydrophilic moieties solvated in the aqueous phase and thus causing the reactant to preferentially accumulate at the droplet surface. Thus it is believed that the reactant in the first mixture tends to rapidly collect at the droplet-continuous phase interface as the emulsion is formed, stabilizing the emulsion and providing a reaction site for the second reactant.

The emulsion of core material in the present method may be performed independent of the wall-forming step, and the first reactant may be introduced to the continuous aqueous phase before or after emulsion. It should be noted that this method differs from potential alternative methods such as those of the Speaker patents previously cited, in which the first wall-forming reactant must be dissolved in the core material, or in a mixture of the core material and a water-immiscible solvent, without the presence of water. Unlike those methods, the present method does not require complete solvation of any wall material in the core phase. Therefore, a wider variety of core materials may be potentially encapsulated by the present inventive method. Because the emulsion step may be performed independent of the wall-forming step, the present inventive method affords greater flexibility with regard to the methods and timing of the emulsion step. Accordingly greater ease of manufacturing is provided by the present inventive method Typically the emulsified state of the core material in the first mixture is maintained by continuous agitation until the second reactant is added and encapsulation is completed. The emulsion may be further stabilized by the use of an emulsifying, wetting, or surfactant agent such as sodium lauryl sulfate, or other materials such as polyethylene glycol esters, sorbitol esters, or similar emulsion-promoting materials either in the continuous phase, or in the core material prior to dispersion.

The emulsion thus prepared is then combined with a second mixture, containing the second, complementary Lewis acid or Lewis base reactant of the wall-forming reaction pair, which may be but need not be amphiphilic. The reactants are complementary in that one is a Lewis acid and the other is a Lewis base and together they react to form an insoluble Lewis acid-Lewis base salt. As used herein the word "complementary" refers to Lewis acids and Lewis bases that react to form insoluble salts. Upon mixing of the emulsion and the second mixture, the second reactant reacts with the first, at least a significant portion of which is believed to be situated at the droplet-water interface. The resulting reaction product, a salt of the Lewis acid Lewis base reactants, precipitates at the droplet interface to form a stabilized wall and thereby microencapsulates the emulsified droplet containing the water-immiscible core material. The precipitation reaction is spontaneous and essentially instantaneous upon mixing of the emulsion and the second mixture at 25° C., and requires no additional heating or curing steps.

Either a Lewis acid reactant or a Lewis base reactant may be used as the first wall reactant dissolved in the continuous phase in which the core material is dispersed. In many embodiments, the Lewis base reactant is used because many of these compounds are also effective emulsifying agents. By contrast, aqueous solutions of suitable Lewis acid compounds may or may not readily emulsify the core material. In either case, and especially when a Lewis acid reactant is used, emulsification of the core material may be facilitated by the addition of a small quantity of an emulsifying agent, such as almost any common surfactant, for example sodium lauryl sulfate.

Generally, microdroplets may be formed by almost any physical method of emulsification. The first reactant is typically dissolved in the aqueous phase prior to such dispersion. However, this is not a requirement, and the first reactant may also be dissolved or partitioned into the aqueous phase after formation of droplets of the core material. In practice, the emulsion is often conveniently stabilized by the first reactant. Typically the second reactant is conveniently added in the form of a prepared aqueous mixture, usually a solution, but it may instead be introduced neat and allowed to dissolve or it may be partitioned into the aqueous phase from some other source, such as a solution of the second reactant in a solvent or introduced in some other manner.

An advantage of the encapsulating salt wall of the instant invention is that it imparts a water-wettable quality to the encapsulated droplet, which may cause the microcapsules to behave as a flocculated suspension, that is to form light, fluffy aggregates. Without wishing to be bound by any particular theory or explanation, it is believed that the flocculated particles aggregate through attractive interaction, but are prevented from caking, or forming dense aggregates, by strong solvation effects, or wetting of the particles. Regardless of the mechanism, the encapsulating wall appears to affect the suspension in a manner similar to the action of flocculating agents, for example sorbitol esters, commonly used to produce similar effects. Flocculating agents are well known in the field of pharmacy, and serve a number of beneficial purposes in preparations of suspended particles and droplets, including controlled sedimentation volume, resistance to caking or breaking instability, and easy dispersion, all of which may be exploited to enhance shelf life stability. The flocculant quality of the microcapsule wall in the instant invention may be increased by inclusion of additional flocculating agents, resulting in compositions that show behavior typical of fully flocculated particulate suspensions.

Some or all effects of additional flocculating agents may be substantially increased by the presence of the capsule wall. Sedimentation volume may be observed to reflect this action. For instance when a particularly buoyant core material is emulsified, the droplets may float to the top, forming a concentrated layer, and possibly re-merge to form a continuous layer. If a flocculating agent is incorporated into such an emulsion, the droplets still float and form a concentrated layer, but they are protected from close interaction by a sheathing solvation layer that increases the volume of the concentrated layer, i.e., the sedimentation volume. If the droplets are further encapsulated using the instant invention, the sedimentation volume, the final volume occupied after settling, typically exceeds that of the emulsion stabilized only by the flocculating agent but lacking the microcapsule wall. The magnitude of this effect varies according to the specific materials used, but a ten to fifty percent increase in sedimentation volume is commonly observed using encapsulation by the instant method when compared with equivalent emulsions lacking such encapsulation.

If the microcapsules contain a core that is liquid at use temperatures, they typically break during application or thereafter, e.g., upon evaporation of the water (if an aqueous carrier is used). On the other hand, robust microcapsules exhibiting little or no breakage may be produced if the core contains a substantial fraction of a solid material. Further, liquid microcapsules may also be stabilized against breakage by specific carrier formulations. Breaking and non-breaking microcapsules will be discussed in more detail later herein.

Shell Wall-Forming Reactants

Substantially any of the wall-forming reactant pairs and adjuvants disclosed in the Speaker et al patents, referred to above, may be utilized in the methods of the present invention. The reactant pairs comprise a Lewis acid reactant and a Lewis base reactant. As used herein, the term "Lewis acid reactant" means a water-solvated ion derived from either a Lewis acid itself or a water-soluble salt of the acid. The term "Lewis base reactant" is analogously defined, wherein water-soluble salts of Lewis bases are defined herein to also include quaternary ammonium salts. Thus, a wall-forming reactant pair may be a combination of the ions of a Lewis acid and of a Lewis base, whether the respective ions may derive from the dissolved acid or base, or the water-soluble salt thereof. Unless otherwise specified, or clear from the context, mention of the presence of a particular Lewis acid or a particular Lewis base as a component of a composition will be understood to encompass either the free acid or base, or the salts of these.

In particular, the Lewis acid reactant may be contributed by any one or a combination of acacia, agar, arabic acid, carboxymethylcellulose, ghatti gum, polyacrylic acid, polyacrylic acid/polyoxyethylene copolymer, sterculia gum, sodium alginate, sodium carboxymethylcellulose, sodium polyacrylate, and sodium polyacrylate cross-linked with polyoxyethylene, alginic acid, pectin or other polyuronic acids, or other acidic gums or salts thereof. Generally any high molecular weight or polymeric Lewis acid reactant makes an effective wall-forming component, and the reactant may comprise one or more acid groups per molecule. If the Lewis acid reactant is used as the first reactant introduced to the dispersed core material, it must be amphiphilic so as to properly associate with both the aqueous phase and the core material.

Sources of the complementary wall-forming Lewis base reactant include benzalkonium chloride, cetylpyridinium chloride, hexylamine, hexanediamine, hexamethylrosanilium chloride, piperidine, triethylamine, triethylenediamine, stearylamine, spermine, and tetramethylrosanilium chloride, or any other similar amine or amine salt capable of precipitating the Lewis acid. These representative Lewis bases are amphiphilic and easily support dispersion of many non-aqueous core materials, and satisfy the requirement of accumulation at the droplet interface. However, the Lewis base need not be amphiphilic if the core material is dispersed in the other aqueous mixture, i.e., the Lewis acid mixture.

Core Materials

Core materials according to the invention may include an active agent, an adjuvant, or both. As used herein, the term "active agent" means a material that performs a primary function of the formulation, such as repelling insects, providing a fragrance, etc. An adjuvant is a material that enhances the efficacy of the active agent, for example by slowing its rate of release or by forming a barrier between the active agent and a surface to which it is applied, such as skin. Other forms of activity modification will be apparent to those of skill in the relevant application areas in which the encapsulated materials are used. It will be appreciated that the distinction between active agent and adjuvant may be somewhat arbitrary in some situations, and that for example a given material may be an adjuvant in some applications while in other applications it may stand alone, and thus be the active agent. Having said that, materials typically used as active agents will now be discussed, followed by a discussion of materials typically used as adjuvants.

The core may comprise an insect or arthropod repellent. For example, DEET (i.e. N,N-diethyl-m-toluamide) may be encapsulated and combined in a carrier composition for aerosol or liquid or creamed fluid topical application, or a soap-like bar. DEET is among the most effective agents used for repelling insects such as mosquitoes and other harmful arthropods such as ticks, and is widely used to prevent their bites and the exposure to infectious disease that may result. Microencapsulated DEET according to the invention has the benefit that the DEET diffuses through the microcapsule wall and evaporates at a controlled rate, providing a relatively long-lasting vapor source of the DEET near the skin of a treated individual. Also, it is to be noted that traditional compositions may not effectively protect against any undesired effects that might result from exposure to DEET. As will be discussed in detail below, the use of certain adjuvants with the microencapsulated DEET may reduce exposure of the underlying skin to the DEET.

A further application of liquid-containing microcapsules, that break upon drying, is to encapsulate a sunscreen agent or solution thereof which is thereby distributed evenly over a skin surface upon drying of the film. Octyl-dimethyl para-amino benzoic acid (Padimate O), is a common liquid sun-protection active ingredient. Padimate O is easily microencapsulated using the methods and materials of the instant invention, and the microcapsules thus formed break upon drying in a manner similar to the silicone oil microcapsules described below. These microcapsules may be included in a blended product containing additionally, for example, a microencapsulated insect repellent or a fragrance. Another common sunscreen agent, 2-hydroxy-4-methoxy-benzophenone (Oxybenzone) is a solid at normal ambient temperatures, and cannot be directly encapsulated in the manner of Padimate O. Oxybenzone may, however, be dissolved in silicone oil or another suitable water-immiscible oil, and the solution may be encapsulated using the methods described for silicone oil below. The resultant capsules break open upon drying in a thin film, distributing the sunscreen agent as desired. Non-breaking capsules containing sunscreen agents may also be produced and may provide a lower risk for skin absorption of the agent. Additionally, the finely divided encapsulated droplets of sunscreen may provide enhancement of sun protection by increasing light scattering, thereby reducing the amount of ultraviolet radiation reaching the skin. Flavorants and fragrances (e.g., limonene and cinnamic aldehyde) may also be microencapsulated according to the invention, as will be discussed in detail below.

Other repellents and/or insecticides may also be incorporated instead of, or in addition to, DEET. These compounds may be similarly encapsulated using the method and materials of the present invention. For example, the compound 1-methylpropyl 2-(2-hydroxyethyl)-1-piperidinecarboxylate (commonly referred to as icaridin or picaridin) is another common lipid-soluble insect repellent, and may be encapsulated using the methods and materials of the instant invention to provide similar benefit. Permethrin is another common insect repellent and insecticide that is similarly lipid-soluble and may be microencapsulated in a similar manner to provide a topical product exhibiting low dermal absorption. Lipid-soluble colorant agents, such as D&C Red #17 dye and similar materials, are also well-suited to encapsulation by these techniques. Encapsulation of lipid-soluble dyes dissolved in an adjuvant material to produce a microcapsule resistant to breakage on drying may produce resulting aqueous suspensions, that when applied to skin, show strong coloration but show much reduced tendency to stain the skin even after drying, because the dyes remain encapsulated. Similarly a core material composed of a colored wax may be encapsulated. Such compositions may for example be used as water-removable cosmetic colorants or face-paints. Conversely, encapsulation of such lipid soluble colorant agents in capsules that rupture upon drying in a thin film may be useful in providing a water-removable quality prior to drying, but releasing the colorant agents for more permanent coloration once the films dries, as for a long-lasting cosmetic colorant or skin-marking agent with a brief period of easy removability following application. Such breakable microcapsules may be produced by using a core material that is liquid at ambient temperature, for example the core material may be prepared by dissolving a lipid-soluble colorant such as D&C Red #17 dye in an encapsulable liquid, such as mineral oil. Combinations of microencapsulated repellents and cosmetic face-paints may be thus formulated, for example to provide a camouflage paint with an intrinsic insect repellent property. Alternately, microencapsulated repellents may simply be compounded as an ingredient in a more standard facepaint formulation.

Adjuvants may be selected to perform any of a variety of functions, including to enhance the physical or chemical stability of the core material and/or the microcapsules in which the core material is encapsulated, and/or to modify the density of the product and/or to control the release rate or diffusion rate of the active agent through the capsular wall and/or to influence the dispersion and/or wetting of the core material during or after the encapsulation process and/or to subsequently affect the carrier phase by diffusing out of the capsule. It is important that any such adjuvant or the combination thereof with other core material not render the core material completely water miscible, that is, at least some part of the core material must remain water immiscible. In some embodiments, preferred adjuvants are those such that the core material is liquid at some elevated temperature, at which the encapsulation reaction is carried out, but solid at some preselected temperature, such as normal ambient temperature (typically about 20° C.). In some cases, it is desired that the core be solid at normal skin temperature, for instance for some cosmetic applications. Suitable adjuvants may include paraffin wax, fatty alcohols, esters of fatty alcohols, glycol ethers of fatty alcohols, triglycerides, polyethylene glycol esters, polyethylene glycol ethers, and fats.

For example, a wax may be combined with DEET in a ratio such that the combination melts, for example, at a temperature of 50° C., and this comprises the core material to be encapsulated. The encapsulation process is then carried out above 50° C., at which temperature the core material is in a liquid state and conducive to emulsification. As the reaction product is returned to normal ambient temperature, the core material solidifies. This Imparts physical robustness to the microcapsule such that it resists deformation, such as experienced during drying in a thin film of dispersed microcapsules. The resulting film may be fully dried and then re-wet without substantial loss of capsule dispersion, because the capsules remain stable and maintain the droplet integrity. In the absence of a solidifying agent, such thin-film drying may in some cases cause deformation and rupture of microcapsules. As adjuvant, the wax further imparts a modified controlled release characteristic as it changes the diffusion rate of the encapsulated DEET out of the capsule. Some adjuvants include solids that melt above the temperature at which the product is to be used (for example, skin temperature in the case of a product for topical application) so that the microcapsule core remains solid in use. This may be useful in cases where it is desired that the microcapsules not break, since the presence of solids in the core (even in the presence also of a liquid) tends to strengthen the microcapsules against crushing.

In many (but not all) applications, the adjuvant must remain miscible with the active agent during dispersion to form suitable droplets, and insufficient miscibility may in some cases be detrimental. For instance, paraffin wax, when used in a DEET-wax combination core, is sufficiently nonpolar that in some core concentrations, water absorbed by DEET on contact with an aqueous continuous phase, such as with the Lewis acid or Lewis base mixture used in encapsulation, causes separation of the paraffin from the DEET to form a separate, third phase. If such a mixture of DEET and paraffin wax is dispersed in an aqueous medium, the droplets formed may not be of uniform composition due to rapid phase separation during mixing. For this reason more polar waxy solids including fatty alcohols such as stearyl alcohol, fatty acid ester or fatty alcohol ester waxes such as cetyl esters wax and other materials with similar polarity, such as polyethylene glycol and polyethylene glycol ethers, are miscible in a greater range of proportions with DEET, and are less prone to separation due to DEET water absorption, and are therefore preferred adjuvants in some applications. Other suitable adjuvants include beeswax, carnauba wax, cholesterol, ethyl stearate, isopropyl myristate, isopropyl palmitate, cetostearyl alcohol, myristyl alcohol, cetyl alcohol, oleyl alcohol, behenyl alcohol, solid hydrogenated castor and vegetable oils, hard and soft paraffins, and hard fats such as tristearin Some appropriate adjuvants, for example polyoxyethylene esters of sorbitol, may also serve an emulsifying and/or flocculation-promoting function. Adjuvants of relatively high polarity, such as for example mixtures of cetearyl alcohol and polyoxyethylene sorbitol esters, may be of use in combination with relatively polar active agents, such as benzyl alcohol (which is roughly ten times as polar as DEET). Other adjuvants include fats and glycol ethers of fatty alcohols.

Additional exemplary adjuvants include silicone oils, one example of which is polydimethyl siloxane (PDMS), commonly known as dimethicone. Moderate-viscosity, low volatility silicone oil products such as Dow Corning 200 form a smooth, non-toxic film when applied to skin. Silicone oils are highly non-polar, and are immiscible with DEET and other similar compounds of moderate polarity. Skin wetted with silicone oil has reduced potential to wetting with DEET and other compounds with which the silicone oil is immiscible, and silicone oil may thus reduce absorption of DEET by the skin. Silicone oil is ordinarily difficult to incorporate into traditional water-based formulations, requiring very fine dispersion and additional dispersing agents and tending to settle and coalesce due to its lower specific gravity relative to water. Silicone oil may however be microencapsulated by the methods and materials of the instant invention to provide a highly stable dispersion.

If no solid component is encapsulated along with the silicone oil, and if the formulation is allowed to dry as a thin film, the microcapsules will typically break open during drying, releasing the contents onto the surface to which the film was applied. By combining a suspension of such silicone oil microcapsules with a suspension of DEET microcapsules that include a solid core adjuvant, a hybrid preparation is formed. When the hybrid preparation is applied and permitted to dry in a thin film, most of the DEET microcapsules remain physically intact, providing insect repellency, while most of the silicone oil microcapsules break open, wetting the surface and the contact area of the DEET microcapsules with silicone oil. The silicone oil film thus produced further reduces the degree of skin contact with the microcapsules containing DEET, and reduces the potential for dermal absorption. A silicone oil film of the type described above may also contribute to protection against, or delay of dermal absorption of, other agents such as plant allergens from poison oak or other rhus species.

While a homogeneous core is often desirable, there is no requirement that the all of the core components remain comiscible during or after dispersion. In fact the ejection of an additional phase or phases due to wetting of one or more core components may be exploited to form multi-phase encapsulated cores such as encapsulated emulsions, slurries, foams, or any other desired mixture. If the core components are miscible prior to dispersion, but separate due to wetting effects as does the paraffin-DEET system described above, a multi-phase core may be generated in-situ, precluding the need for a separate blending step.

Isolation/Use of Microencapsulated Materials

Microencapsulated compounds (such as DEET) may be used and applied exactly as produced following formation of capsules, but the composition may be further improved by mixing the capsules into a carrier composition such as an aqueous 1% polyethylene glycol solution which may aid in uniform application of the product, adhesion of the capsules to the skin surface, and may inhibit dermal absorption of the active agent, and also may impart a desirable "feel" characteristic. Additionally, upon drying of the composition in a film, for instance as applied to skin, the polyethylene glycol is deposited surrounding the microcapsules, and may stabilize capsules against breakage and modify the release characteristic in a manner similar to encapsulated adjuvants described above. In other specific embodiments it may be preferable to concentrate, dry, or otherwise harvest the microcapsules from the aqueous continuous mixture, and in some cases to re-suspend them in a different carrier composition.

The suspended microcapsules as generated by the reaction process described above may then be subjected to harvesting and/or concentration and/or resuspension, and/or further dispersion into a carrier composition by any of the following or other means:

a) Direct dispersion of the entire product suspension into a carrier composition, as by pouring and mixing the entire contents of the microencapsulation reaction vessel into a volume of a separate carrier composition, for instance a 1% solution of polyethylene glycol;

b) Concentration (for example by filtration, sedimentation or centrifugation), of the newly formed microcapsules out of the reaction mixture, and removal of the bulk of the continuous phase to form a mass or aggregate of the microcapsules, which may be re-suspended in a new carrier composition, or rinsed by repeated concentration/resuspension cycles prior to a final resuspension and drying to a powder state;

c) Partition of the microcapsules from the formative mixture into a carrier composition of a different phase, for instance by bringing the newly formed microcapsule suspension into contact with a non-aqueous phase such as dichloromethane which may attract them into suspension in this phase, such that the non-aqueous phase may then be decanted or otherwise removed from contact with the aqueous phase, and the microcapsules subsequently concentrated as described in (b) above or (d) below;

d) Evaporation (for example by air-drying, freeze-drying, spray-drying or other means) of the suspending medium followed by re-dispersal of the microcapsules in the carrier composition, for instance by spraying the newly formed microcapsule suspension into an rising stream of dry air, droplets containing populations of microcapsules may dry into small granules of microencapsulated material that may be subsequently resuspended in a new carrier composition;

e) Any other means of effecting the dispersion of the microcapsules into a carrier composition suitable for an intended use.

Some forms of capsules, particularly those formulated to break open during drying in a thin film may not be suitable for drying as in b or d above, but the more robust embodiments of the instant invention readily survive even multiple cycles of drying and re-suspension. A suspension of capsules robust to drying may be fully evaporated to dryness to form a cake or bar that may be used much like a bar of soap, to apply microcapsules to wet skin. In particular, use of a carrier mixture that includes a stearate, for example sodium stearate, with subsequent concentration by drying, may produce a soap-like bar that may be rubbed against wet skin to distribute microcapsules re-suspended as the dry carrier dissolves against the wet skin. In some embodiments of the invention, the microcapsules may be used in aqueous compositions such as lotions, crèmes, or sprayable compositions, for example for cosmetic, pharmaceutical, or other uses. In some embodiments, the microcapsules may be incorporated, along with the associated water in droplets containing the microcapsules, into an oil phase to make a water-in-oil emulsion crème or lotion or ointment.

Microcapsules may be further dispersed in a carrier composition designed to permit uniform application of the microcapsules to a surface such as skin, and to adhere the capsules to the surface, and may include other agents that impart other desirable characteristics. Various materials may be included in the carrier fluid to modify the properties of the carrier itself. Additional carboxymethylcellulose may be added to alter the rheological properties of the fluid, for instance to inhibit stratification due to microcapsule density. Methylcellulose or other appropriate materials may be added to contribute a thermal viscosity change or gelation property. Some polyethylene glycols, for instance PEG 3350, alter the carrier rheology making the microcapsule suspension more sprayable, and additionally contribute to lowering product freezing point as well as to reduce the availability of encapsulated DEET (and/or other active agents) for dermal absorption. Generally, the microcapsule suspension may be introduced to a wide variety of carrier materials which may impart a similarly broad spectrum of additional properties.

Viscous oils, such as medium viscosity mineral oils, constitute one set of carrier materials capable of imparting substantially different properties to microencapsulated materials. By use of materials such as SPAN 80 surfactant, well known to aid in production of stable water-in-oil type emulsions, it is possible to disperse an aqueous suspension of microcapsules in an oil base. The result of such dispersion is an oil-based ointment, consisting of a continuous phase of mineral oil, in which are dispersed fine droplets of the aqueous carrier of the microcapsule suspension, in which are suspended microcapsules. Such a dispersion may be produced using ordinary ointment formulating methods, such that microcapsules suspended in tiny aqueous droplets dispersed in the oil phase are clearly visible under a typical laboratory light microscope. The resulting ointment provides high resistance to wash-off, and the aqueous carrier droplets serve to control release of the active material. If such an ointment is made with microcapsules containing DEET, the release of encapsulated DEET to the continuous oil phase is substantially limited by the low (around 1%) solubility of DEET in water. The aqueous phase serves as a bottleneck layer to concentration-driven diffusion processes, resulting in a very long-lasting repellent product suitable for use on skin which will be submerged or repeatedly exposed to water, and may be appropriate for use in repelling water-borne pests.

Another example of a carrier component that may provide added benefit is a water-soluble sunscreen component such as phenylbenzimidazole sulfonic acid, or a skin protectant such as aloe vera extract. Finely divided zinc oxide or bentonite clay may similarly be incorporated, to provide sun-protective or blemish-concealing or other functions. These compounds and others may be combined with the carrier base material to lend additional cosmetic or other qualities to the formulation.

A specific additional application involves the reduction of percutaneous absorption of a fragrance compound or other odorant, e.g., for the topical delivery of perfumes and cosmetics in a manner similar to its capability as a repellent. Reduced skin absorption by the same mechanism discussed above may be of importance in such applications as well. Similarly, these products and methods may be useful as delivery vehicles for fragrance enhancers generally, such as those used to provide a certain odor to commercial products, such as soaps etc. For example, cinnamic aldehyde is a useful and inexpensive compound in widespread use that provides a floral scent to soaps and other products. Unfortunately it is well known that this compound is a dermal sensitizer, generating allergic reactions in many consumers. For this reason, it is undesirable to use the compound in applications in which it would be directly applied to skin. Cinnamic aldehyde is representative of a wide range of fragrance compounds, especially aldehydes and alcohols that tend to oxidize to the corresponding aldehydes. Mixing of such microencapsulated compounds with microencapsulated adjuvants that are capable of providing a barrier layer on the skin, such as silicone oil as described above, may reduce the availability of the compounds for dermal absorption, and thus reduce the risk of allergic response due to contact with these compounds. Inclusion and/or co-encapsulation of preservatives or compounds protective against oxidation may also prolong the useful shelf life of products containing these compounds.

Microencapsulation with adjuvants chosen to extend release may also provide useful long-duration qualities to highly volatile fragrance agents, such as limonene and other terpenes. Limonene, a staple citrus-type fragrance in common use, evaporates very rapidly, and the odor is almost undetectable within an hour of application to skin. Limonene may be directly microencapsulated using the methods and materials of the instant invention, but without use of an adjuvant, the fragrance is prolonged little. If limonene is microencapsulated in a core-adjuvant formulation, the duration of fragrance can be extended to more than one hour. Limonene is well solvated by cetyl esters wax, polyethylene glycol and esters of polyethylene glycol, paraffin wax, and silicone oil, among other materials suitable as core adjuvants. Limonene's volatility is so great, however, that even doubling the duration through use of an adjuvant-enhanced microcapsule, the fragrance still dissipates rapidly.

A further increase of release duration for limonene (or other active agents) may be realized through a multiphase encapsulated product, in which two (or more) mutually immiscible adjuvants are included. At least one of the adjuvants is miscible with the active agent. For example, silicone oil and cetyl esters wax (liquid at 50° C.; other fatty acid ester or fatty alcohol ester waxes may also be used) are mutually immiscible due to large differences in polarity. If an active agent, for example, limonene, is introduced into, for example, a mixture of silicone oil and liquefied cetyl esters wax, the agent will partition between the two immiscible oil phases. The phases may then be co-dispersed to form an oil-in-oil emulsion, the differences in polarity maintaining separation of the two oil phases. If this emulsion is then subsequently dispersed as droplets into an aqueous phase, a super-emulsion is formed, having droplets of one oil phase dispersed in the interior of droplets of a second oil phase, which are themselves dispersed in the aqueous phase. If this mixture is microencapsulated by the methods of the instant invention, the resulting product is a suspension of microencapsulated solid microspheres of a moderately polar wax which contain additional microdroplets of a non-polar liquid with an agent, such as limonene, partitioned in both oil phases inside the microcapsule. Other emulsions containing different proportions of polar and non-polar adjuvant ingredients may be similarly formed, exhibiting various interior structures, including large single droplets and multiple small droplets. The additional phase boundaries inside the microcapsule may provide an enhanced barrier to diffusion, further limiting the evaporation rate. This preparation extends the duration of limonene fragrance to multiple hours, depending upon what materials are used. Additionally, the strength of the limonene aroma is greatly reduced at application, since most of the limonene is trapped inside the microcapsule preparation, and it evaporates slowly over time. A mixture of microcapsule types having different core compositions, e.g., some relatively fast-release and some relatively slow release microcapsules, may provide a more even limonene delivery rate for the product. This approach may be used for other active agents as well.

Cinnamic aldehyde is less volatile than limonene, and if a mixture of cinnamic aldehyde and limonene is directly applied to skin in the absence of microencapsulated formulations, the limonene scent is initially overwhelmingly dominant and then rapidly fades. A suitable balance of fragrance elements occurs only briefly when much of the limonene has evaporated. By contrast, a mixture of microcapsules of cinnamic aldehyde including an adjuvant that provides moderately extended release with microcapsules of limonene including two immiscible adjuvants as described above greatly extends the duration of time during which the fragrance elements contribute at comparable levels to the overall product scent.

Many volatile fragrances may be encapsulated in this manner, according to the invention. Other microencapsulated materials may also be employed as flavorants in chewing gums. The flavorants need not be volatile. Other exemplary flavorants include isoamyl acetate, ethyl cinnamate, ethyl propionate, ethyl butanoate, ethyl hexanoate, and similar esters, methyl salicylate, menthol, and capsaicin. In fact, typically any flavoring or fragrance ingredient that may be dispersed in an oil droplet may be encapsulated using the instant methods and materials.

EXAMPLES

Example 1

DEET-Containing Microcapsules

An aqueous solution A of 0.1%, by weight, sodium carboxymethylcellulose (NaCMC, Amend Drug and Chemical Company, Inc., New York, N.Y.) is prepared by pre-wetting 0.1 gram of NaCMC with about 0.5 mL acetone, then adding about 90 mL water. The mixture is heated to 50° C., and the solution is stirred until all NaCMC is dissolved to form a clear, colorless solution. The acetone rapidly evaporates out of the solution, which is subsequently cooled to room temperature and further diluted with sufficient water to reach a total volume of 100 mL.

An aqueous solution B containing 0.05% benzalkonium chloride is prepared by diluting 0.1 mL of 50% concentrated benzalkonium chloride in aqueous solution (Spectrum Chemical Manufacturing Corporation, Gardena, Calif.) to a final volume of 100 mL.

A 1.0 mL volume of DEET to be encapsulated is introduced to a 10.0 mL volume of solution B and dispersed by agitation, coacervation, or any other emulsion-forming mixing techniques known to those skilled in the art. An emulsion is formed, wherein amphiphilic benzalkonium ions partition to interfacial regions between the DEET droplets and the surrounding aqueous solution.

A 10.0 mL volume of solution A is added to the emulsion thus formed containing dispersed microdroplets of DEET in Solution B. The mixture is further agitated to mix the components, exposing the microdroplets to the complementary wall-forming component. Ideally the emulsion is continually agitated during addition of solution A.

Microencapsulation occurs almost instantaneously, and the resulting composition is an aqueous suspension of microencapsulated DEET. The capsules thus formed are shelf-stable, showing no evidence of Ostwald ripening or coalescence after months of storage. Some stratification of the suspension is observable after more than one month, due to microcapsule buoyancy, but the microcapsules are readily returned to uniform suspension by minor agitation, such as a simple swirl of the container.

Example 2

Sprayable DEET-Based Insect Repellent

A composition is prepared as in example 1, and is further dispersed into an additional 10 mL of carrier composition of 1% aqueous polyethylene glycol 3350 or other water-soluble polyethylene glycol to form an easily applied, sprayable product possessing a pleasant feel. The polyethylene glycol helps the microcapsules adhere to the skin, and also helps provide desirable feel characteristics. The composition thus applied is detectable by a light odor of DEET that persists for several hours, but unlike other applications of dissolved or emulsified DEET products, does not lend an oily texture to the skin, nor does it obviously mar or stain clothing. Additionally this composition is readily removed by washing with soap and water, leaving no noticeable odor. A variation of this Example is to incorporate polyethylene glycol also (or instead) in the core material prior to encapsulation, so that it subsequently diffuses into the carrier during or after the encapsulation process. This reduces the internal capsule volume and/or renders the core material porous, while introducing polyethylene glycol into the carrier.

Stock solutions for use in Examples 3-7 are prepared as follows:

Sodium CMC Solution 1%
1. Carboxymethylcellulose Sodium [CMC] (Amend) 1 g per 100 mL solution desired.
2. Wet CMC with isopropyl alcohol 70%, sufficient to form loose slurry.
3. Stir continuously while slowly adding 80 mL purified water per 100 mL final volume.
4. Resulting solution will be lumpy and gummy.
5. Heat to boiling and stir rapidly for 2 hours open to atmosphere, to volatilize alcohol.
6. Some film formation at surface may occur.
7. Add 10 mL purified water, and stir, covered, for an additional 30 minutes to dissolve any film formed.
8. Dilute to final volume and store in closed container.

Benzalkonium Chloride Solution 1%
1. Benzalkonium Chloride Solution 50% (Spectrum) 2 mL (per 100 mL solution desired).
2. Stir continuously while adding 80 mL (per 100 mL solution desired) hot (80° C.) purified water.
3. Stir continuously while adding hot (80° C.) purified water.
4. Stir rapidly for 30 minutes open to atmosphere, to volatilize alcohol (~5% of base) from 50% base solution.
5. Dilute to final volume, cool, and store in closed container.

Example 3

DEET-Based Insect Repellent Crème—30% DEET

Core Composition:

| | |
|---|---|
| DEET (Morflex) | 150.0 g |
| Cetostearyl alcohol (Cognis) | 85.0 g |
| PEG 6000 Distearate (Spectrum) | 5.0 g |
| DC-200 Silicone (Dow Corning) | 5.0 g |
| PEG 3350 (Spectrum) | 25.0 g |
| SPAN 60 (Spectrum) | 5.0 g |
| TWEEN 60 surfactant (Spectrum) | 5.0 g |

Solution A:

| | |
|---|---|
| Sodium CMC solution 1% | 50.0 g |
| Water | 145.0 g |

Solution B:

| | |
|---|---|
| Benzalkonium chloride solution 1% | 25.0 g |

Method of Preparation:
1. In a 500 mL wide-mouth glass container, heat all Core ingredients except DEET to melting (~70° C.) and stir to mix completely. Maintain heat and rapid stirring.
2. Add DEET to other Core ingredients, and heat and stir until fully incorporated into a uniform melt solution. (Some cloudiness may be present.) Increase stirring speed to high magnetic stirrer RPM (nominal 700 cm/s shear).
3. Warm Solution A to a similar (~70° C.) temperature, and slowly add to stirring Core mixture over about 1 minute. Initially Solution A will be emulsified in the Core phase as a water-in-oil type emulsion. As addition of Solution A continues, the emulsion will undergo inversion to an oil-in-water type, producing finer and more uniform droplets than possible by directly dispersing Core in Solution A. Additionally PEG 3350 will partition from the Core phase into the aqueous phase during dispersion, and is primarily a carrier phase component.
4. Slowly add full volume of Solution B, over about 30 seconds duration, and permit complete mixing by maintaining rapid stirring for an additional 120 seconds. Discontinue stirring and remove from heat.
5. Transfer resulting mixture to a container with a secure screw cap, and cool, periodically agitating the contents until ambient temperature is achieved. If agitation during cooling is insufficient, creaming due to capsule buoyancy can cause inhomogeneous thickening. An additional warming-cooling cycle can recover the batch if inhomogeneous thickening is observed.

Example 4

Sprayable DEET-Based Insect Repellent—30%

Core Composition:

| | |
|---|---|
| DEET (Morflex) | 150.0 g |
| Myristyl Alcohol (Cognis) | 10.0 g |
| Cetyl Esters Wax (Spectrum) | 5.0 g |
| PEG 3350 (Spectrum) | 20.0 g |
| SPAN 60 (Spectrum) | 5.0 g |
| TWEEN 60 surfactant (Spectrum) | 5.0 g |

Solution A:

| | |
|---|---|
| Sodium CMC solution 1% | 50.0 mL |
| Water | 230.0 mL |

Solution B:

| | |
|---|---|
| Benzalkonium chloride solution 1% | 25.0 mL |

Method of Preparation:
1. In a 500 mL wide-mouth glass container, heat all Core ingredients except DEET to melting (~70° C.) and stir to mix completely. Maintain heat and rapid stirring.

2. Add DEET to other Core ingredients, and heat and stir until fully incorporated into a uniform melt solution. (Some cloudiness may be present.) Increase stirring speed to high magnetic stirrer RPM (nominal 700 cm/s shear).
3. Warm Solution A to a similar (~70° C.) temperature, and slowly add to stirring Core mixture over about 1 minute. Initially Solution A will be emulsified in the Core phase as a water-in-oil type emulsion. As addition of Solution A continues, the emulsion will undergo inversion to an oil-in-water type, producing finer and more uniform droplets than possible by directly dispersing Core in Solution A. Additionally PEG 3350 will partition from the Core phase into the aqueous phase during dispersion, and is primarily a carrier phase component.
4. Slowly add full volume of Solution B, over about 30 seconds duration, and permit complete mixing by maintaining rapid stirring for an additional 120 seconds. Discontinue stirring and remove from heat.
5. Transfer resulting mixture to a container with a secure screw cap, and cool, periodically agitating the contents until ambient temperature is achieved. If agitation during cooling is insufficient, creaming due to capsule buoyancy can cause inhomogeneous thickening. An additional warming-cooling cycle can recover the batch if inhomogeneous thickening is observed.

Example 5

DEET-Based Insect Repellent Bar—10%

Core Composition:

| DEET (Morflex) | 100.0 g |
| Cetostearyl Alcohol (Cognis) | 50.0 g |
| SPAN 60 (Spectrum) | 5.0 g |
| TWEEN 60 surfactant (Spectrum) | 5.0 g |

Solution A:

| Sodium CMC solution 1% | 225.0 mL |
| Water | 450.0 mL |

Solution B:

| Benzalkonium chloride solution 1% | 25.0 mL |

Solidifier:

| Sodium Stearate | 315.0 g |

Method of Preparation:
1. Prepare microcapsules as for crème formulations, mixing Core and Solution A, and then adding Solution B, but do not proceed to cooling step.
2. Maintain heat and stirring of microcapsule suspension, and slowly add Solidifier about one tenth at a time, allowing the solids to fully incorporate and disperse in the stirring mixture.
3. When all of the Solidifier has been incorporated, the resulting mixture may be poured into a sheet or mold and permitted to cool. The mixture sets to a firm soap consistency, and may be packaged directly, or further dried to increase firmness and decrease weight.

Example 6

Oil-Based DEET Insect Repellent Formulation—10%

Core Composition:

| DEET (Morflex) | 150.0 mL |
| Cetostearyl alcohol (Cognis) | 65.0 g |
| SPAN 60 (Spectrum) | 5.0 g |
| TWEEN 60 surfactant (Spectrum) | 5.0 g |

Solution A:

| Sodium CMC solution 1% | 50.0 mL |
| Water | 200.0 |

Solution B:

| Benzalkonium chloride solution 1% | 50.0 mL |

Oil Carrier:

| Mineral Oil (Spectrum) | 975.0 g |
| SPAN 80 (Spectrum) | 25.0 g |

Method of Preparation:
1. Prepare microcapsules as for crème formulations, mixing Core and Solution A, and then adding Solution B.
2. Stir Oil Carrier ingredients to fully dissolve SPAN 80 in Mineral Oil.
3. Slowly add microcapsule suspension to stirring Oil Carrier solution, allowing water-based microcapsule suspension to disperse and emulsify into Oil Carrier.
4. Stir until mixture is uniform in appearance.

Example 7

Limonene Fragrance Formulation—10%

Core Phase A:

| Limonene (Morflex) | 50.0 g |
| DC 200 (Dow Corning) | 25.0 g |

Core Phase B:

| Myristyl Alcohol (Cognis) | 120.0 g |
| PEG 3350 (Spectrum) | 20.0 g |
| SPAN 60 (Spectrum) | 5.0 g |

| -continued | |
|---|---|
| TWEEN 60 surfactant (Spectrum) | 5.0 g |

Solution A:

| | |
|---|---|
| Sodium CMC solution 1% | 50.0 mL |
| Water | 200.0 |

Solution B:

| | |
|---|---|
| Benzalkonium chloride solution 1% | 25.0 mL |

Method of Preparation:
1. In a 500 mL wide-mouth glass container, heat all Core Phase B ingredients to melting (~60° C.) and stir to mix completely. Maintain heat and rapid stirring.
2. Mix all Core Phase A ingredients completely, and slowly add Core Phase A ingredients to Core Phase B melt. Core Phase A emulsifies into Core Phase B melt. The emulsion thus formed is referred to as Core Emulsion Mixture.
3. Warm Solution A to a similar (~70° C.) temperature, and slowly add to stirring Core Emulsion Mixture over about 1 minute. Initially Solution A will be emulsified in the Core Emulsion Mixture as a water-in-oil type emulsion. As addition of Solution A continues, the emulsion will undergo inversion to an oil-in-water type, producing finer and more uniform droplets than possible by directly dispersing Core Emulsion Mixture in Solution A. Additionally PEG 3350 will partition from the Core Phase B into the aqueous phase during dispersion, and is primarily a carrier phase component.
4. Slowly add full volume of Solution B, over about 30 seconds duration, and permit complete mixing by maintaining rapid stirring for an additional 120 seconds. Discontinue stirring and remove from heat.
5. Transfer resulting mixture to a container with a secure screw cap, and cool, periodically agitating the contents until ambient temperature is achieved.

The compositions of this invention may be readily manufactured and are well suited for use in the applications described herein, as well as others. The simple mixing steps involved in the methods of their preparation make them particularly adaptable to scaling to an industrial continuous-flow process. As exemplified herein, such methods may be performed in the absence of organic solvents, thereby obviating potential health and environmental concerns.

Thus an improvement is provided to existing preparations for superficial application of active agents, particularly vaporizable ones and especially ones for which it is desired to minimize contact with and/or absorption into the underlying surface. Further, the methods and compositions of this invention tend to preserve the desirable structure of an emulsion through the physical formation of the encapsulating wall, permitting use of specific advantageous carrier compositions without loss of commercial shelf life. In particular, the instant invention has useful application as a means to provide a useful insect repellent formulation containing DEET as a microencapsulated active component but minimizing actual skin contact with DEET itself, thereby limiting the potential for dermal transport and absorption.

Although the invention is illustrated and described herein with reference to specific embodiments, it is not intended that the subjoined claims be limited to the details shown. Rather, it is expected that various modifications may be made in these details by those skilled in the art, which modifications may still be within the spirit and scope of the claimed subject matter and it is intended that these claims be construed accordingly.

The invention claimed is:

1. Microcapsules containing a water-immiscible core material, wherein the microcapsules are produced by a method comprising:
    (a) forming an emulsion comprising droplets of a water-immiscible core material in a first aqueous solution of an amphiphilic first wall-forming reactant that preferentially accumulates at the surface of the droplets;
    (b) forming a second aqueous solution of a second wall-forming reactant; and
    (c) combining the emulsion with the second aqueous solution to permit a reaction between the first and second reactants such that the resulting reaction product forms an encapsulating wall surrounding the core material of each emulsion droplet to encapsulate a core consisting of the water-immiscible core material;
wherein one of said first and second reactants comprises a Lewis base reactant and the other comprises a Lewis acid reactant, wherein the reaction product consists of a salt of the Lewis base-Lewis acid reactant pair, wherein the method of forming the microcapsules is performed in the absence of organic solvents and the microcapsules are free of organic solvents, and wherein the water-immiscible core material comprises a material selected from the group consisting of flavorants, silicones, triglycerides, waxes, and vaporizable active agents selected from the group consisting of fragrances, insect repellents and arthropod repellents.

2. Microcapsules as recited in claim 1, wherein the encapsulating wall surrounds each emulsion droplet to encapsulate a core consisting of the water-immiscible core material.

3. Microcapsules as recited in claim 2, further comprising a carrier composition.

4. Microcapsules as recited in claim 2, wherein the core material comprises a vaporizable active agent.

5. Microcapsules as recited in claim 4, wherein the core material comprises at least two mutually immiscible, water-immiscible adjuvants, at least one of which is miscible with the vaporizable active agent.

6. Microcapsules as recited in claim 4, wherein the vaporizable active agent is an insect repellent or arthropod pest repellent.

7. Microcapsules as recited in claim 4, wherein the vaporizable active agent is DEET.

8. Microcapsules as recited in claim 2, wherein the core material comprises a silicone oil.

9. Microcapsules comprising (a) a shell comprising the salt product of a Lewis acid reactant and a Lewis base reactant, and (b) contained within the shell, a water-immiscible core material comprising a vaporizable active agent; wherein the microcapsules are formed in the absence of organic solvents and are free of organic solvents, where the shell encapsulates the core and the core consists of the water-immiscible core material, and wherein the water-immiscible core material comprises a material selected from the group consisting of flavorants, silicones, triglycerides, waxes, and vaporizable active agents selected from the group consisting of fragrances, insect repellents and arthropod repellents.

10. Microcapsules as recited in claim 9, wherein the vaporizable active agent is a fragrance or flavorant.

11. Microcapsules as recited in claim 9, wherein the vaporizable active agent is an insect repellent or arthropod pest repellent.

12. Microcapsules as recited in claim 1, wherein the core further comprises a colorant and wherein the microcapsules break upon drying to release the colorant.

13. A granulated material comprising microcapsules as recited in claim 1.

14. A sprayable composition comprising microcapsules as recited in claim 1.

15. The sprayable composition as recited in claim 14, wherein the sprayable composition comprises a continuous phase comprising polyethylene glycol.

16. The sprayable composition as recited in claim 14, wherein the sprayable composition is aqueous and wherein the core comprises DEET.

17. An emulsion comprising a carrier phase and droplets dispersed therein, wherein the droplets comprise an aqueous phase and microcapsules as recited in claim 1.

18. A composition comprising the emulsion as recited in claim 17, wherein the microcapsules contain a volatile agent.

19. The composition as recited in claim 18, wherein the composition comprises an insect repellent.

20. The composition as recited in claim 19, wherein the insect repellent is DEET.

21. Microcapsules as recited in claim 1, wherein the core comprises two or more immiscible phases.

22. A method of treating skin to apply an active agent or combination of agents, the method comprising applying to the skin a composition including microcapsules as recited in claim 9.

23. A composition as recited in claim 9 comprising at least two populations of microcapsules, wherein the core material of a first population of microcapsules comprises an active agent and the core material of a second population of microcapsules is immiscible with the active agent.

24. The composition as recited in claim 23, wherein the active agent is DEET and the core material of the second population of microcapsules comprises a silicone oil.

25. Microcapsules as recited in claim 9 said core material comprising benzyl alcohol and a second component selected from fatty alcohols, polyoxyethylene sorbitol esters, and combinations of these.

26. The sprayable composition as recited in claim 14, wherein the sprayable composition is aqueous and wherein the core comprises a sunscreen.

27. The sprayable composition as recited in claim 14, wherein the sprayable composition is aqueous and wherein the core comprises 2-hydroxy-4-methoxy- benzophenone.

28. The sprayable composition as recited in claim 14, wherein the sprayable composition is aqueous and wherein the core comprises octyl-dimethyl para-amino benzoic acid.

29. Microcapsules as recited in claim 1, wherein the core material comprising a flavorant.

* * * * *